United States Patent [19]

Kawata et al.

[11] Patent Number: 4,594,240
[45] Date of Patent: Jun. 10, 1986

[54] SHEET-SHAPE ADHESIVE PREPARATION

[75] Inventors: Terushige Kawata; Shinsuke Yamashita, both of Tokushima, Japan

[73] Assignees: Teikoku Seiyaku Kabushiki Kaisha, Kagawa; Nippon Kayaku Kabushiki Kaisha; Kaken Pharmaceutical Co., Ltd., both of Tokyo, all of Japan

[21] Appl. No.: 530,070

[22] Filed: Sep. 7, 1983

[30] Foreign Application Priority Data

Oct. 10, 1982 [JP] Japan ................... 57-158588

[51] Int. Cl.4 .............. A61F 13/00; A61L 15/03; A61K 9/70
[52] U.S. Cl. .................................................. 424/28
[58] Field of Search ............... 424/28; 427/2; 433/24

[56] References Cited

U.S. PATENT DOCUMENTS

| 2,563,593 | 8/1951 | Engel | 424/28 |
|---|---|---|---|
| 2,693,438 | 11/1954 | Ward | 424/28 |
| 3,287,222 | 11/1966 | Carde et al. | 424/28 |
| 3,339,546 | 9/1967 | Chen | 424/28 |
| 3,598,122 | 8/1971 | Zaffaroni | 424/28 |
| 3,632,740 | 1/1972 | Robinson et al. | 424/28 |
| 3,731,683 | 5/1973 | Zaffaroni | 424/28 |
| 3,742,951 | 7/1973 | Zaffaroni | 424/28 |
| 3,754,332 | 8/1973 | Warren | 424/28 |
| 3,972,995 | 8/1976 | Tsuk et al. | 424/28 |
| 4,136,162 | 1/1979 | Fuchs et al. | 424/28 |
| 4,180,558 | 12/1979 | Goldberg et al. | 424/28 |
| 4,197,289 | 4/1980 | Sturzenegger et al. | 424/27 |
| 4,210,633 | 1/1980 | Takruri et al. | 424/28 |
| 4,250,163 | 2/1981 | Nagai et al. | 424/28 |
| 4,292,299 | 9/1981 | Suzuki et al. | 424/28 |
| 4,332,789 | 6/1982 | Mlodozeniec | 424/27 |
| 4,349,531 | 9/1982 | Mlodozeniec et al. | 424/27 |
| 4,483,846 | 12/1984 | Koide et al. | 424/19 |

FOREIGN PATENT DOCUMENTS

| 822075 | 9/1969 | Canada | 424/28 |
|---|---|---|---|
| EP106107 | 4/1984 | European Pat. Off. | 424/28 |
| 52-18813 | 2/1977 | Japan | 424/28 |
| 55-62014 | 5/1980 | Japan | 424/28 |
| 56-161058 | 12/1981 | Japan | 424/28 |

OTHER PUBLICATIONS

Derwent An-83-742560134, Xram C83-07959, ONO Pharmaceutical KK Koide, T, Sasatani, S, Inaba, K, EP-86093; J58134019.

Primary Examiner—Shep K. Rose
Attorney, Agent, or Firm—Birch, Stewart, Kolasch & Birch

[57] ABSTRACT

A sheet-shape adhesive preparation for promoting tooth-movement in orthodontics comprising a layer of a pharmaceutical composition containing as the active ingredient a prostaglandin (e.g. prostaglandin $E_1$, prostaglandin $E_2$, and prostaglandin $F_{2\alpha}$) in admixture with one or more high molecular weight compounds and a flexible base sheet, a process for the preparation thereof, and a method for promoting tooth-movement in orthodontics by applying the sheet-shape adhesive preparation to the mucous membrane of gingiva. Said preparation can be kept for a long period of time without being dissolved in saliva and without irritation or unpleasant feeling when applied to the mucous membrane of gingiva and hence can show the tooth-movement activity of the active prostaglandin for a long period of time.

5 Claims, No Drawings

SHEET-SHAPE ADHESIVE PREPARATION

The present invention relates to a sheet-shape adhesive preparation for promoting tooth-movement in orthodontics, more particularly, it relates to a preparation for promoting tooth-movement containing as an effective ingredient a prostaglandin which comprises a layer of a pharmaceutical composition containing a prostaglandin in the sheet-like form and a flexible base sheet, said agent being able to adhere well onto the mucous membrane of gingiva and to be retained on the gingiva for a long period of time without being dissolved and disintegrated with saliva and hence without being swallowed.

Prostaglandins, particularly prostaglandin $E_1$, prostaglandin $E_2$, and prostaglandin $F_{2\alpha}$, are extracted from spermatocyst of humans and sheep or are derived from the natural substance and are well utilized as a medicine because of their potent pharmacological activities. Focusing on their muscular contraction activity, the present inventors have intensively studied the application thereof to orthodontics in order to promote tooth-movement.

In the treatment of various oral diseases, such as pyorrhea, stomatitis and toothache, various medicines are usually applied within oral cavity in the form of an ointment or liquid preparation. However, these application methods are not suitable for exhibiting activity of the active ingredient for a long period of time because the preparations are dissolved in saliva and are swallowed within a short period of time.

Recently as a new type of application form, it is proposed to apply a medicine onto a skin in the form of skin preparations such as a tape preparation, paste, or cataplasma preparation.

The present inventors have tried to apply the prostaglandin to gingiva in the form of a preparation similar to the above skin preparations in order to promote tooth-movement in orthodontics. However, gingiva is always wet with saliva, and hence, the preparation which is applicable to the skin is hardly applicable to the mucous membrane of gingiva because of various problems. For instance, cataplasma preparations usually have a high water content such as 50 to 60% by weight, and hence, they are less adhesive on the mucous membrane of gingiva and are easily peeled off. Furthermore, cataplasma preparations give an unpleasant feeling when applied, because they have a large thickness. On the other hand, tape preparations are usually incorporated with a strong adhesive with less water content, and hence, show too strong of adhesion to gingiva, which induces injury of gingiva. Further, they rapidly became wet with saliva resulting in shortly loosing adhesion, and hence, they can not be retained on the mucous membrane of gingiva for a long priod of time.

The present inventors have extensively studied on an improved preparation applicable to the mucous membrane of gingiva which can be retained on the gingiva for a long period of time without being dissolved in saliva and without giving irritation or unpleasant feeling in order to use a prostaglandin as an agent for promoting tooth-movement in orthodontics. As a result, it has been found that a preparation comprising a layer of a pharmaceutical composition containing a prostaglandin and a flexible base sheet is suitable because it can be retained within the oral cavity for a long period of time without being affected with saliva and further the prostaglandin contained therein can effectively be absorbed to promote the tooth-movement.

An object of the present invention is provide a preparation for promoting tooth-movement in orthodontics, which contains a prostaglandin as an effective ingredient. Another object of the invention is to provide an improved preparation applicable to the mucous membrane of gingiva, which comprises a layer of a pharmaceutical composition comprising one or more prostaglandins and one or more high molecular weight compounds which is laminated onto a flexible base sheet. A further object of the invention is to provide a method for promoting tooth-movement in orthodontics, which comprises applying a prostaglandin to the mucous membrane of gingiva in the form of a sheet-like adhesive preparation. These and other objects and advantages of the invention will be apparent to persons skilled in the art from the following description.

The preparation for promoting tooth-movement in orthodontics of the present invention comprises a sheet-like layer of a pharmaceutical composition containing a prostaglandin as the active ingredient in admixture with one or more high molecular weight compounds and a flexible base sheet.

The base sheet used in the present invention includes non-woven fabric made from nylon, vinylon, etc., lints, papers, polyvinyl chloride film, polyurethane film, ethylene-vinyl acetate copolymer film, or other synthetic polymer films, which are flexible. Materials having poor water-resistance such as paper may be coated with a protecting coating layer. The thickness of the base sheet is not critical, but a preferred base sheet is as thin as possible in order to avoid an unpleasant feeling when applied to the mucous membrane of gingiva, for example, a thickness of 10 to 100$\mu$, more preferably 20 to 70$\mu$.

The high molecular weight compounds used for the pharmaceutical composition include water-soluble high molecular weight compounds and water-insoluble high molecular weight compounds.

The water-soluble high molecular weight compounds are classified into two groups: (1) those compounds having a low dissolution rate in water, such as gelatin, alubumin, karaya gum, agar and gluten, and (2) those compounds having a high dissolution rate in water, such as polyacrylic acid salts (e.g. sodium polyacrylate or ammonium polyacrylate), cellulose derivatives (e.g. hydroxyethyl cellulose or sodium carboxymethyl cellulose), sodium alginate, starch, polyvinyl alcohol, polyvinylpyrrolidone. In addition, these groups of compounds are preferably used together. In the present specification, "a water-soluble high molecular weight compound having a low dissolution rate in water" means such a compound that when said compound (1 g) is formed into a sheet in a thickness of 0.1 mm, the formed sheet is uniformly dissolved in water (1 liter) at 37° C. in a period of more than 10 minutes, preferably more than 30 minutes, and "a water-soluble high molecular weight compound having a high dissolution rate in water" means such a compound that a formed sheet (thickness: 0.1 mm) prepared likewise is uniformly dissolved in water (1 liter) at 37° C. within 10 minutes, preferably within 5 minutes.

The water-insoluble high molecular weight compounds used for the pharmaceutical composition include, for example, vinyl acetate resin and cellulose derivatives (e.g. ethyl cellulose, propyl cellulose, ethylmethyl cellulose, cellulose acetate phthalate).

These high molecular weight compounds are preferably used in combination of one or more water-soluble high molecular weight compounds having a low dissolution rate in water, one or more water-soluble high molecular weight compounds having a high dissolution rate in water, and one or more water-insoluble high molecular weight compounds. A preferred combination is a combination of a water-soluble high molecular weight compound having a low dissolution rate in water selected from gelatin, alubumin, karaya gum, agar and gluten; a water-soluble high molecular weight compound having a high dissolution rate in water selected from polyacrylic acid salts (e.g. sodium polyacrylate or ammonium polyacrylate), cellulose derivatives (e.g. hydroxyethyl cellulose, sodium carboxymethyl cellulose), sodium alginate, starch, polyvinyl alcohol, and polyvinylpyrrolidone; and a water-insoluble high molecular weight compound selected from vinyl acetate resin and cellulose derivatives (e.g. ethyl cellulose, propyl cellulose, ethylmethyl cellulose, cellulose acetate phthalate).

The water-soluble high molecular weight compounds having a low dissolution rate in water are effective for forming gel having excellent shape-retention and hence are incorporated in order to prolong adhesion time of the product and to gradually release the active ingredient. In order to promote the shape-retention, it is further preferable to incorporate a water-insoluble high molecular weight compound in addition to the water-soluble high molecular weight compound having a low dissolution rate in water. When the compound having a low dissolution rate and the water-insoluble high molecular weight compound are used in too small of an amount, the final product shows less shape-retention and is easily disintegrated. But on the other hand, when they are used in an excess amount, the final product shows less adhesion and is easily peeled off when applied. Besides, the water-soluble high molecular weight compounds having a high dissolution rate in water are effective for improvement of adhesion. When the compound having a high dissolution rate is used in a too small of an amount, the final product shows less adhesion and hence is easily peeled off when applied. On the other hand, when it is used in an excess amount, the final product shows too high of an swelling rate and hence is easily disintegrated.

The water-soluble high molecular weight compounds having a low dissolution rate and the water-insoluble high molecular weight compounds are incorporated in a total amount of 20 to 70% by weight based on the total weight of the pharmaceutical composition (in dry state). The ratio of the water-insoluble high molecular weight compound and the water-soluble high molecular weight compound having a low dissolution rate is in the range of 1:9 to 6:4 by weight, preferably 2:8 to 5:5 by weight. The water-soluble high molecular weight compounds having a high dissolution rate in water are incorporated in an amount of 5 to 50% by weight, preferably 10 to 40% by weight, based on the total weight of the pharmaceutical composition (in dry state).

The pharmaceutical composition containing prostaglandins per se should preferably be flexible in order to apply the preparation to curved area of gingiva. For this purpose, the pharmaceutical composition is preferably incorporated with a softening agent such as glycerin, propylene glycol, polyethylene glycol, 1,3-butanediol, sorbitol, or the like, which may be used alone or in combination of two or more thereof. Particularly preferred as a softening agent is glycerin or propylene or a mixture thereof. The softening agent is usually incorporated in an amount of 5 to about 50% by weight, preferably 10 to 30% by weight, based on the total weight of the pharmaceutical composition (in dry state). When the softening agent is used in a too large amount, it is penetrated out from the layer of the pharmaceutical composition, which results in inferior retention stability of the final product. On the other hand, when the amount is too small, the pharmaceutical composition becomes hard and occassionally cracks, and hence, the final product shows less adhesion onto the mucous membrane of gingiva.

The pharmaceutical composition can be prepared by a conventional method, for example, by dissolving one or more water-soluble high molecular weight compounds having a low dissolution rate in water at an elevated temperature (e.g. at 70° to 90° C.), adding thereto one or more water-insoluble high molecular weight compounds with stirring at an elevated tempertureone, further adding one or more water-soluble high molecular weight compounds having a high dissolution rate in water at an elevated temperature to give a homogeneous aqueous mixture, and then, preferably after cooling to a somewhat lower temperature (e.g. about 50° C.), adding an aqueous solution of a prostaglandin and optionally a preservatice (e.g. methylparaben, propylparaben) in a softening agent to give a pharmaceutical composition containing as an active ingredient a prostaglandin. In the above procedure, the purified water is usually used in an amount of 10 to 100 parts by weight per 100 parts by weight of the high molecular weight compounds.

The prostaglandins used in the preparation include all of natural and synthetic prostaglandins and derivatives thereof having muscular constriction activity, for example, prostaglandin $E_1$, prostaglandin $E_2$, and prostaglandin $F_{2\alpha}$. Particularly preferred is prostaglandin $F_{2\alpha}$. These prostaglandins are used alone or in combination of two or more thereof and are used in an amount of 1 to 1,000 μg, preferably 10 to 100 μg, per one $cm^2$ of the final sheet-like preparation. In other measure, the prostaglandins are incorporated in an amount of 0.002 to 2% by weight, preferably 0.02 to 1% by weight, based on the total weight of the pharmaceutical composition.

The pharmaceutical composition may also be incorporated with other conventional additives such as sweeting agents, flavors, colorants, etc.

The pharmaceutical composition thus prepared is spread on a base sheet and dried to form a layer of the pharmaceutical composition in the sheet-like state. The thickness of the layer of the pharmaceutical composition is not critical, but is usually in the range of 50 to 2,000μ, preferably 200 to 1,000μ (in dry state, i.e. when dried until water content thereof becomes about 5 to 20% by weight). The laminated product thus prepared is cut into the desired size.

The agent for promoting tooth-movement in orthodontics as prepared above comprises a layer of a pharmaceutical composition and a flexible base sheet and is dried until the water content thereof becomes in not more than 20% by weight, preferably 5 to 15% by weight. The dry-state product has no surface tackiness and, hence it is not necessary that it be coated with a protecting coating layer. But from hygienic viewpoint, the product is preferably covered with a protecting film such as polyethylene film or cellophane film on the layer of a pharmaceutical composition, which is peeled off when used.

A preferred sheet-shape adhesive preparation for applying to gingiva of the present invention comprises (A) a layer of a pharmaceutical composition comprising (1) 0.02 to 1% by weight of a prostaglandin, (2) 15 to 40% by weight of one or more water-soluble high molecular weight compounds having a low dissolution rate in water selected from the group consisting of agar, gelatin, karaya gum and gluten, (3) 10 to 35% by weight of one or more water-soluble high molecular weight compounds having a high dissolution rate in water selected from the group consisting of an alkali metal salt of polyacrylic acid, an alkali metal salt of alginic acid, an alkali metal salt of carboxymethyl cellulose, polyvinyl alcohol and polyvinylpyrrolidone, (4) 10 to 30% by weight of one or more water-insoluble high molecular weight compounds selected from vinyl acetate resin, (5) 10 to 30% by weight of a softening agent selected from the group consisting of glycerin, propylene glycol, polyethylene glycol, 1,3-butanediol and sorbitol, and (6) 5 to 15% by weight of water, said amount of these components (1) to (6) being based on the total weight of the pharmaceutical composition in dry state, and (B) a flexible base sheet.

The preparation of the present invention is easily handled because there is no surface tackiness as mentioned above, but on the other hand, when it is applied onto the mucous membrane of gingiva, it adsorbs saliva and adheres well thereto owing to the action of the water-soluble high molecular weight compounds contained in the pharmaceutical composition. Furthermore, it can be retained on the gingiva for a long period of time, such as several to about 20 hours, without being disintegrated with saliva. Thus, the agent of the present invention is effective for making prostaglandins absorb through gingiva continuously, by which teeth are effectively moved, and hence, the desired correction of irregularity of the teeth and malocclusion in orthodontics can effectively be done.

The present invention is illustrated by the following Examples but is not construed to be limited thereto.

EXAMPLE 1

A sheet-like adhesive preparation for promoting tooth-movement is prepared in the following formulation:

| Component | Part by weight |
| --- | --- |
| Vinyl acetate resin | 20.0 |
| Agar | 5.0 |
| Sodium polyacrylate | 20.0 |
| Gluten | 25.0 |
| Polyvinylpyrrolidone | 20.0 |
| Purified water | 178.68 |
| Karaya gum | 3.0 |
| Prostaglandin $F_{2\alpha}$ | 0.1 |
| Polyethylene glycol 400 | 20.0 |
| Methylparaben | 0.17 |
| Propylparaben | 0.05 |
| Sodium carbonate | 8.0 |

Agar, gluten and karaya gum are dissolved in purified water at 90° C., and to the aqueous solution is added vinyl acetate resin with well stirring in a kneader, and the mixture is dispersed well above 70° C. To the dispersion are added sodium polyacrylate and polyvinylpyrrolidone, and the mixture is homogeneously mixed. After cooling the mixture to 50° C., a solution of prostaglandin $F_{2\alpha}$, methylparaben and propylparaben in polyethylene glycol 400 is added thereto, and the mixture is homogeneously mixed to give a paste. The thus obtained paste mixture is spread onto a non-woven fabric in a ratio of 500 g/m² and then dried at room temperature until the water content becomes 8% by weight. The dried product is cut in a size of 4 cm × 1 cm to give the desired sheet-shape adhesive product.

EXAMPLE 2

A sheet-like adhesive preparation for promoting tooth-movement is prepared in the following formulation:

| Component | Part by weight |
| --- | --- |
| Vinyl acetate resin | 20.1 |
| Agar | 7.0 |
| Polyvinylalcohol | 7.0 |
| Polyvinylpyrrolidone | 2.1 |
| Purified water | 198.5 |
| Karaya gum | 23.1 |
| CMC Na | 7.0 |
| Gluten | 10.0 |
| Prostaglandin $F_{2\alpha}$ | 0.1 |
| Polyethylene glycol 400 | 13.0 |
| Sorbitol (70% aqueous solution) | 7.0 |
| Sodium carbonate | 5.1 |

The above components are homogeneously mixed in the same manner as described in Example 1, and the mixture is spread onto a non-woven fabric in a ratio of 500 g/m² and then dried at room temperature until the water content becomes 8% by weight. The dried product is cut in a size of 4 cm × 1 cm to give the desired sheet-shape adhesive product.

EXAMPLE 3

A sheet-like adhesive preparation for promoting tooth-movement is prepared in the following formulation:

| Component | Part by weight |
| --- | --- |
| Vinyl acetate resin | 20.0 |
| Gelatin | 10.0 |
| Polyvinylpyrrolidone | 30.0 |
| Purified water | 193.8 |
| CMC Na | 6.0 |
| Sodium polyacrylate | 5.0 |
| Sodium alginate | 10.0 |
| Prostaglandin $F_{2\alpha}$ | 0.1 |
| Glycerin | 20.0 |
| Sodium carbonate | 5.1 |

The above components are homogeneously mixed in the same manner as described in Example 1, and the mixture is spread onto a non-woven fabric in a ratio of 500 g/m² and then dried at room temperature until the water content becomes 8% by weight. The dried product is cut in a size of 4 cm × 1 cm to give the desired sheet-shape adhesive product.

EXAMPLE 4

A sheet-like adhesive preparation for promoting tooth-movement is prepared in the following formulation:

| Component | Part by weight |
| --- | --- |
| Vinyl acetate resin | 15.0 |

-continued

| Component | Part by weight |
| --- | --- |
| Gelatin | 10.0 |
| Gluten | 25.0 |
| Agar | 5.0 |
| Polyvinylalcohol | 10.0 |
| Purified water | 188.9 |
| Sodium alginate | 10.0 |
| CMC Na | 10.0 |
| Prostaglandin $F_{2\alpha}$ | 1.0 |
| 1,3-Butandiol | 5.0 |
| Sorbitol | 15.0 |
| Sodium carbonate | 5.1 |

The above components are homogeneously mixed in the same manner as described in Example 1, and the mixture is spread onto a non-woven fabric in a ratio of 500 g/m² and then dried at room temperature until the water content becomes 8% by weight. The dried product is cut in a size of 4 cm × 1 cm to give the desired sheet-shape adhesive product.

CLINICAL TESTS (1) The sheet-shape adhesive product (0.7 cm × 1.5 cm) prepared in the same manner as described in Example 2 was applied to 11 patients (male, ages: 8 to 25 years old) with malocclusion of class I, II and III in Angle's classification. In all patients, distal movement of canine teeth and labial movement of front teeth were tried by conventional edgewise appliances and the sheet-shape paste product was applied onto gingiva at the labial side of the patients every night before went to bed. The treatment was continued for one month, and the tooth-movement was observed. The results are shown in the following table.

| Age of patient | Distal movement of canine teeth | Labial movement of anterior teeth |
| --- | --- | --- |
| 25 | +++ | +++ |
| 14 | ++ | ++ |
| 10 | +++ | +++ |
| 14 | + | + |
| 8 | ++ | + |
| 8 | + | + |
| 14 | +++ | +++ |
| 11 | ++ | ++ |
| 12 | ++ | ++ |
| 10 | 0 | 0 |
| 9 | ++ | ++ |

[Note]
+++: Tooth-movement was significantly rapidly achieved (within 30 days)
++: Tooth-movement was rapidly achieved (within 60 days)
+: Tooth-movement was achieved but it was usual speed as in case of using an ordinary promoting agent.
0: No effect of tooth-movement was observed.

(2) Treatment of male patient with reversed occlusion:

The male patient (age: 12 years and 7 months) with reversed occulsion was treated by conventional edgewise appliance for the purpose of affecting distal movement of 3|3 teeth and labial movement of 2-|-2 teeth, wherein a sheet-shape adhesive preparation (prostaglandin $F_{2\alpha}$ content: 17 μg/cm²) prepared in the same manner as described in Example 2 was applied to the labial gingiva of 3-|-3 teeth every night. As a result, after about one and half month, the desired tooth-movement was achieved.

(3) Treatment of female patient with reversed occlusion:

The female patient (age: 9 years and 6 months) with reversed occlusion was treated by conventional FKO (removable appliance) for improving over bite of anterior teeth, wherein a sheet-shape adhesive preparation (prostaglandin $F_{2\alpha}$ content: 25 μg/cm²) prepared in the same manner as described in Example 2 was applied to the labial gingiva of 2|2 teeth every night. As a result, after about one month, the over bite was remarkedly improved.

(4) Treatment of male patient with reversed occlusion accompanying with stenosed maxillary dental arch:

The male patient (age: 14 years and 4 months) was treated by inserting a quad helix arch to the 7|7 teeth and also inserting a transverse loop to the 6|6 teeth for spreading the maxillary dental arch, for affecting distal movement of 3|3 teeth and for affecting movement of 6|6 teeth toward baccal side, wherein a sheet-shape adhesive preparation (prostaglandin $F_{2\alpha}$ content: 25 μg/cm²) prepared in the same manner as described in Example 2 was applied to only right gingiva (as a control, left gingiva was not applied to by the prostaglandin preparation). As a result, after about one month, the dental arch on right side was spread, but not the dental arch on the left side.

What is claimed is:

1. A sheet-shape adhesive preparation for promoting tooth-movement in orthodontics, which comprises
   (A) a flexible base sheet comprised of a non-woven fabric of nylon, vinylone, lints, papers, polyvinyl chloride film, polyurethane film, ethylene-vinyl acetate copolymer film, or flexible synthetic polymer films, and
   (B) a layer of a pharmaceutical composition containing
      (a) a 0.002 to 2% by weight of a prostaglandin,
      (b) 5 to 50% by weight of a water-soluble high molecular weight compound having a high dissolution rate in water selected from the group consisting of sodium polyacrylate, ammonium polyacrylate, hydroxyethyl cellulose, sodium carboxymethyl cellulose, sodium alginate, starch, polyvinyl alcohol and polyvinylpyrrolidone,
      (c) totally 20 to 70% by weight of (i) a water-insoluble high molecular weight compound selected from the group consisting of vinyl acetate resin, ethyl cellulose, propyl cellulose, ethylmethyl cellulose and cellulose acetate phthalate and (ii) a water-soluble high molecular weight compound having a low dissolution rate in water selected from the group consisting of gelatin, alubumin, karaya gum, agar and gluten, the ratio of said water-insoluble high molecular weight compound and water-soluble high molecular weight compound having a low dissolution rate being in the range of 1:9 to 6:4 by weight,
      (d) 5 to 50% by weight of a softening agent, and
      (e) 5 to 20% by weight of water on the flexible base sheet.

2. A sheet-shape adhesive preparation for promoting tooth-movement in orthodontics in accordance with claim 1 which comprises
   (A) a flexible base sheet having water resistance in accordance with claim 1 and
   (B) a layer of a pharmaceutical composition containing
      (a) a 0.002 to 2% by weight of a $E_1$ prostaglandin,
      (b) 5 to 50% by weight of a water-soluble high molecular weight compound having a high dissolution rate in water selected from the group consisting of sodium polyacrylate, ammonium polyacrylate, hydroxyethyl cellulose, sodium carboxymethyl cellulose, sodium alginate, starch, polyvinyl alcohol and polyvinylpyrrolidone, (c) totally 20 to 70% by weight of (i) a water-insoluble high molecular weight compound selected from the group consisting of vinyl acetate resin, ethyl cellulose, propyl cellulose, ethylmethyl cellulose and cellulose acetate phthalate and (ii) a water-soluble high molecular weight compound having a low dissolution rate in water selected from the group consisting of gelatin, alubumin, karaya gum, agar and gluten, the ratio of said water-insoluble high molecular weight compound having a low dissolution rate being in the range of 1:9 to 6:4 by weight, (d) 5 to 50% by weight of a softening agent, and (e) 5 to 20% by weight of water on the flexible base sheet.

3. A preparation according to claim 1, wherein said prostaglandin is at least one member selected from the group consisting of prostaglandin $E_1$, prostaglandin $E_2$ and prostaglandin $F_{2\alpha}$.

4. A sheet-shape adhesive preparation according to claim 1, wherein said layer of a pharmaceutical composition comprises:

(a) 0.02 to 1% by weight of a $F_{2\alpha}$ prostaglandin;

(b) 15 to 40% by weight of one or more water-soluble high molecular weight compounds having a low dissolution rate in water selected from the group consisting of agar, gelatin, karaya gum and gluten;

(c) 10 to 35% by weight of one or more water-soluble high molecular weight compounds having a high dissolution rate in water selected from the group consisting of an alkali metal salt of polyacrylic acid, an alkali metal salt of alginic acid, an alkali metal salt of carboxymethyl cellulose, polyvinyl alcohol and polyvinylpyrrolidone;

(d) 10 to 30% by weight of vinyl acetate resin as a water-insoluble high molecular weight compound;

(e) 10 to 30% by weight of a softening agent selected from the group consisting of glycerin, propylene glycol, polyethylene glycol, 1,3-butanediol and sorbitol; and (f) 5 to 15% by weight of water, said amount of these components (a) to (f) being based on the total weight of the pharmaceutical composition in a dry state.

5. A sheet-shape adhesive preparation for promoting tooth-movement in orthodontics, in accordance with claim 1 which comprises (A) a flexible base sheet, in accordance with claim 1 and (B) a layer of a pharmaceutical composition containing (a) a 0.002 to 2% by weight of a $E_2$ prostaglandin, (b) 5 to 50% by weight of a water-soluble high molecular weight compound having a high dissolution rate in water selected from the group consisting of sodium polyacrylate, ammonium polyacrylate, hydroxyethyl cellulose, sodium carboxymethyl cellulose, sodium alginate, starch, polyvinyl alcohol and polyvinylpyrrolidone, (c) totally 20 to 70% by weight of (i) a water-insoluble high molecular weight compound selected from the group consisting of vinyl acetate resin, ethyl cellulose, propyl cellulose, ethylmethyl cellulose and cellulose acetate phthalate and (ii) a water-soluble high molecular weight compound having a low dissolution rate in water selected from the group consisting of gelatin, alubumin, karaya gum, agar and gluten, the ratio of said water-insoluble high molecular weight compound and water-soluble high molecular weight compound having a low dissolution rate being in the range of 1:9 to 6:4 by weight, (d) 5 to 50% by weight of a softening agent, and (e) 5 to 20% by weight of water on the flexible base sheet, said sheet-shape preparation having no surface tackiness and being capable of adsorbing saliva for promoting adherence to gingiva.

* * * * *